United States Patent
Takacs

[19]
[11] Patent Number: 6,162,054
[45] Date of Patent: Dec. 19, 2000

[54] SUBGINGIVAL JAW IMPLANT

[76] Inventor: Gyula Takacs, Bahnhofstr. 27, 99450, Coburg, Germany

[21] Appl. No.: 09/237,443
[22] Filed: Jan. 26, 1999

[30] Foreign Application Priority Data

Jan. 28, 1998 [DE] Germany .................. 198 03 172

[51] Int. Cl.[7] .................................................. A61C 8/00
[52] U.S. Cl. ................................................... 433/174
[58] Field of Search .................................. 433/173, 174

[56] References Cited

U.S. PATENT DOCUMENTS

| | | | |
|---|---|---|---|
| 4,293,302 | 10/1981 | Hassler et al. | 433/173 |
| 4,468,200 | 8/1984 | Münch | 433/174 |
| 4,746,293 | 5/1988 | Lundgren et al. | 433/173 |
| 4,793,808 | 12/1988 | Kirsch | 433/173 |
| 4,850,873 | 7/1989 | Lazzara et al. | 433/173 |
| 4,863,383 | 9/1989 | Grafelmann | 433/174 |
| 5,006,069 | 4/1991 | Lazzara et al. | 433/174 |
| 5,174,755 | 12/1992 | Fukuda | 433/173 |
| 5,368,483 | 11/1994 | Sutter et al. | 433/173 |
| 5,417,568 | 5/1995 | Giglio | 433/174 |

Primary Examiner—Ralph A. Lewis
Attorney, Agent, or Firm—Pearne & Gordon LLP

[57] ABSTRACT

The invention relates to a subgingival jaw implant with an anchor body 4 which is made of metal material and at whose one end there is a surface 5 which is provided with a profile for engagement of a screwing instrument and on which a tooth replacement support 7 with a corresponding mating surface 14 can be supported. In order to permit particularly good incorporation of the jaw implant from the periodontal point of view, the invention provides that the surface 5 has a crest 12 and two flanks 12a, 12b descending therefrom, and the maximum diameter D1 of the tooth replacement support 7 is equal to or smaller than the maximum diameter D2 of the surface 5.

15 Claims, 4 Drawing Sheets

SUBGINGIVAL JAW IMPLANT

BACKGROUND OF THE INVENTION

The invention relates to a subgingival jaw implant with a metal anchor body on which a tooth replacement support can be supported.

Such a jaw implant is known from EP 0 747 017 A2. There, a cylindrical anchor body which can be screwed into the jawbone has, at one end, a surface with a raised hexagon profile. A threaded bore is provided in the hexagon profile. Supported on the surface there is a tooth replacement support, which is secured by means of a compression anchor screw which engages in the threaded bore. The tooth replacement support has a surrounding flange, on the upper side of which there bears the lower edge of a tooth crown received thereon.

The known jaw implant has the disadvantage that the anchor body can come loose in the bone even in the event of a light impact on the tooth crown. A further disadvantage is that a gingival pocket forming around the screwed-in anchor body does not have an optimum shape from the periodontal point of view. In particular, no papilla, or ginigival elevation, is formed in the interspace between the implanted tooth and the healthy tooth. As a result, the adjacent healthy tooth is susceptible to periodontitis.

EP 0 111 134 A1 further discloses a transgingival jaw implant with an anchor body made of ceramic material. During the incorporation phase, the anchor body of this implant penetrates the gingival epithelium, which settles on a radially surrounding groove of the anchor body. The protruding anchor stump is uncomfortable for the patient. Due to constant mechanical stresses acting on the anchor stump during incorporation, the direct one fusion with the surface of the anchor body, which is absolutely essential for an optimum hold, does not take place, i.e. there is no osseointegration. Here, the implant becomes incorporated in the bone by the agency of a layer of connective tissue. The layer of connective tissue has the disadvantage that it allows infections to enter. Because of the brittleness of the ceramic material, it is not possible to fix a tooth replacement support by means of a screw. The tooth replacement support has to be cemented onto the anchor body. This makes it difficult to repair such a jaw implant. Moreover, in the event of an impact on the tooth replacement, the anchor body may break. Changing a broken anchor body is expensive.

BRIEF SUMMARY OF THE INVENTION

The object of the present invention is to provide a jaw implant which ensures an improved hold and is as safe as possible from the periodontal point of view.

According to the invention, the surface has a crest and two flanks descending therefrom, and the maximum diameter of the tooth replacement support is equal to or smaller than the maximum diameter of the surface. The embodiment of the surface according to the invention results in the formation of an improved gingival pocket from the periodontal point of view. In particular, a papilla is in each case formed between the implanted tooth and adjacent healthy teeth. The hold of the jaw implant is improved by means of the dimensioning of the tooth replacement support in relation to the surface.

The profile can be expediently an internal and external hexagon profile. This permits the use of conventional screwing instruments for screwing the anchor body into the alveolar ridge.

A threaded bore can be provided within the profile in order to receive a screw for securing the tooth replacement support on the anchor body.

The crest can be perpendicular to the axis of the threaded bore, the flanks advantageously descending from the crest at an angle of 10 to 20°. The crest and the flanks can also be constituent parts of an arch of the surface. This is of particular periodontal advantage.

According to another embodiment feature, a projection is provided on the flank. Moreover, a further crest can be provided on the crest. The abovementioned measures guarantee a perfectly centered fit of a tooth replacement support received on the surface.

The tooth replacement support can, at a first end, have a mating surface corresponding to the surface, preferably with a recess corresponding to the further crest. The mating surface can have a further recess corresponding to the projection. This ensures a reliable and perfect fit of the tooth replacement support on the surface of the anchor body. According to a further embodiment feature, the tooth replacement support is made in one piece.

The tooth replacement support can have, in proximity to the corresponding mating surface, a projection extending at least in sections. A tooth replacement received on the tooth replacement support advantageously bears with its lower circumferential edge on the projection. In the event of an impact on the tooth replacement, the forces introduced are in part carried off to the surface via the projection.

The maximum diameter of the tooth replacement support advantageously decreases from the first end toward the second end. This facilitates fitting of the tooth replacement.

An external thread, tapering conically in the direction of the other end, can be provided at least in sections on the outside of the anchor body for the purpose of engagement in the jawbone. This results in a particularly firm hold in the jawbone.

According to a further embodiment feature, the metal material can be titanium or stainless steel.

BRIEF DESCRIPTION OF THE SEVERAL VIEWS OF THE DRAWING

An illustrative embodiment of the invention is explained in greater detail below with reference to the drawing, in which.

DETAILED DESCRIPTION OF THE INVENTION

Figure 1:
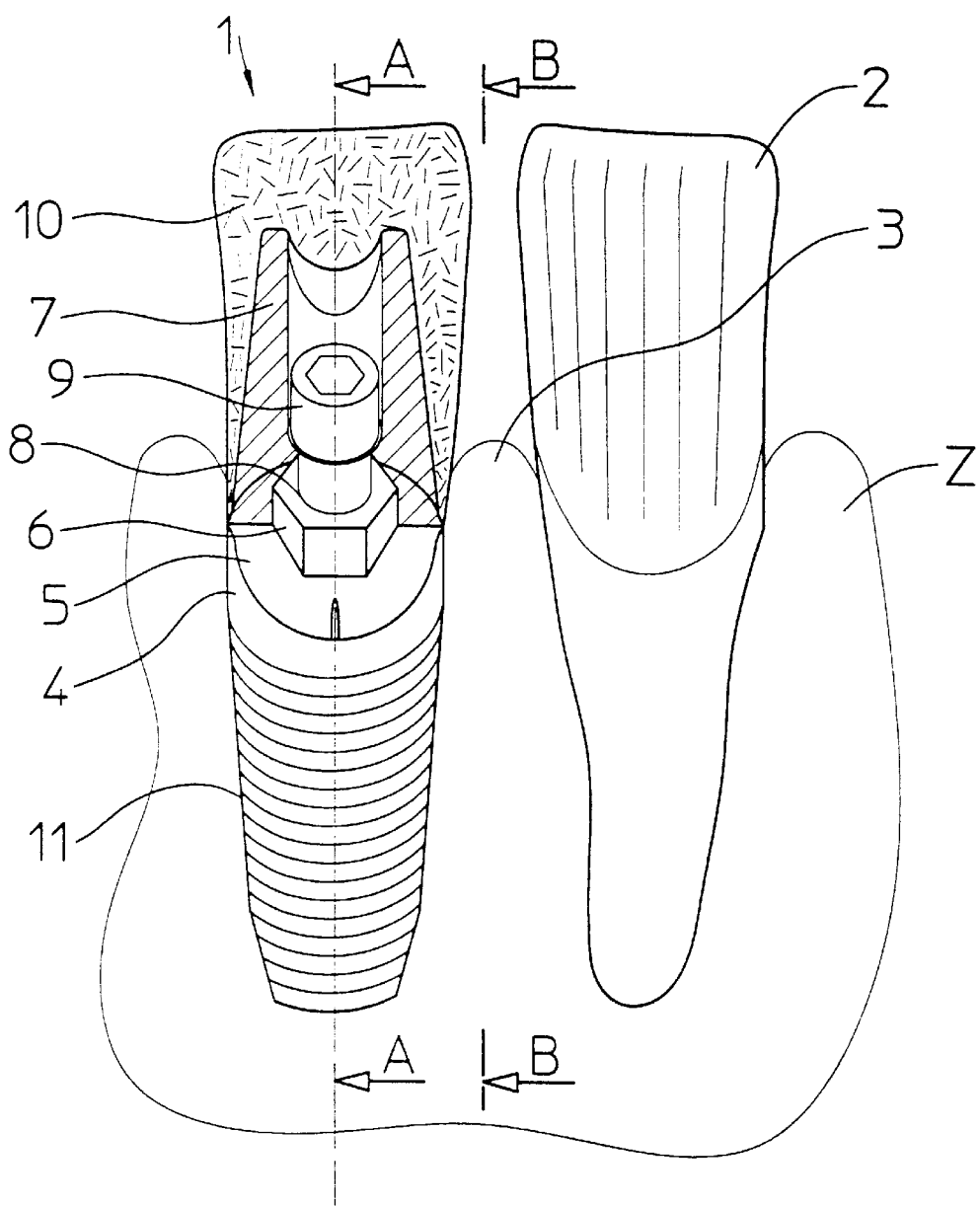
FIG. 1 shows a partial perspective view of a jaw implant.

FIG. 1 shows, in a partial perspective view, a jaw implant 1 alongside a healthy tooth 2. The gum Z forms a gingival elevation 3, the so-called papilla, between them.

The jaw implant 1 has an anchor body 4 with a surface 5. Jutting out from the surface 5 there is an external hexagon profile 6 on which a wrench can be applied for screwing the anchor body 4 into the jawbone. A one-piece tooth replacement support 7 is held on the anchor body 4 by means of a compression anchor screw 9 which is received in a threaded bore 8. A tooth crown 10 is received on the tooth replacement support 7.

On the outside of the anchor body 4 there is a conically tapering external thread 11. The maximum diameter of the tooth replacement support 7 is indicated by D1, while that of the surface 5 is indicated by D2.

Figure 2:
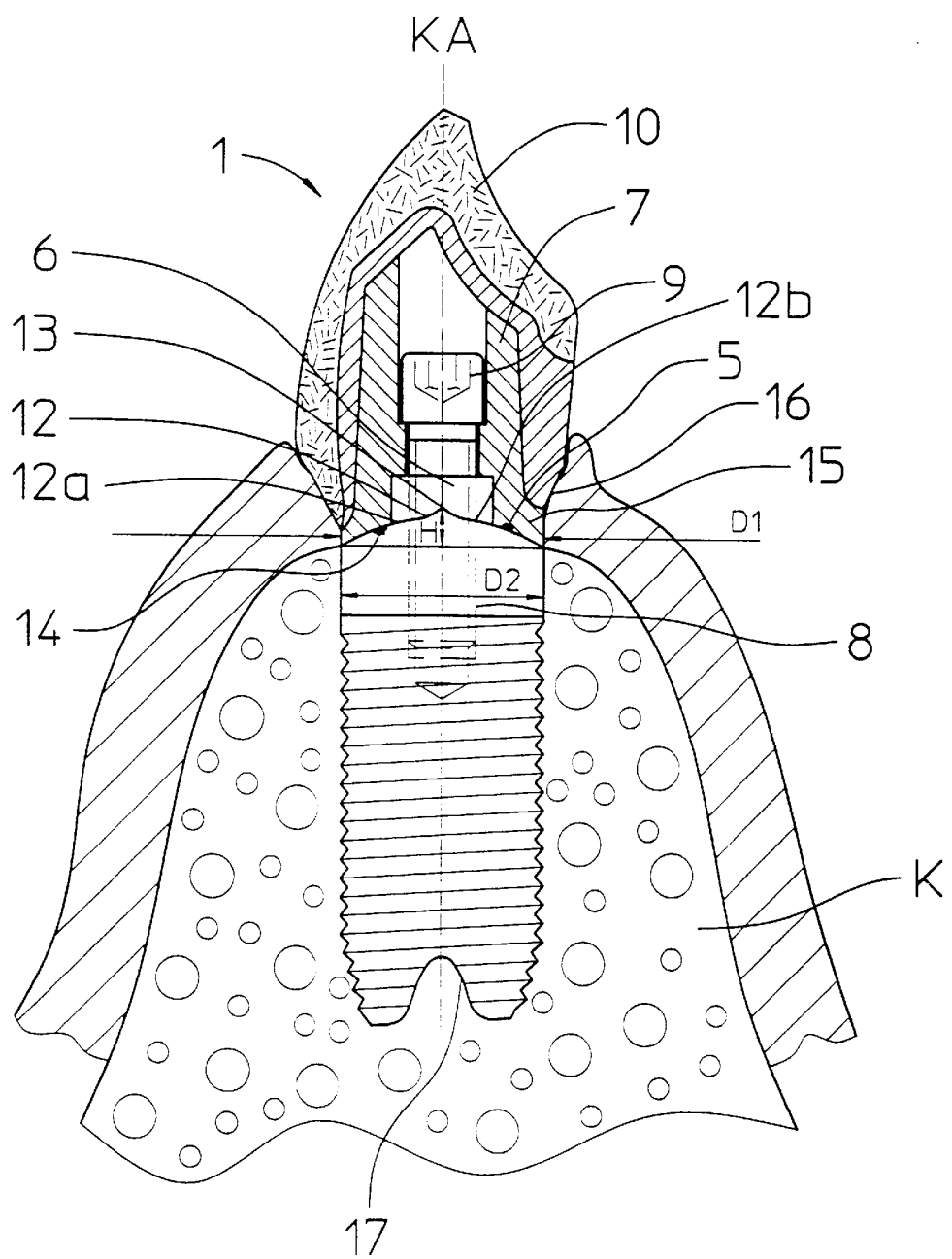
FIG. 2 shows a section along the line A—A in FIG. 1.

FIG. 2 shows a section along the line A—A in FIG. 1. The surface 5 is here designed in the form of a saddle, on the crest 12 of which a further smaller crest 13 is integrally formed. The height of the saddle in relation to the horizontal is indicated by H. The axis of the crest 12 is here perpendicular to the axis KA of the threaded bore 8. To the left and right of the crest 12 are the flanks 12a and 12b which descend from the crest 12 at an angle of about 15°.

The tooth replacement support 7 lies with a correspondingly shaped mating surface 14 on the surface 5. It has, in proximity to the mating surface 14, a circumferential projection 15. The circumferential edge 16 of the tooth crown 10 is supported on the circumferential projection 15. The tooth crown 10 is secured on the tooth replacement support 7 by means of a locking screw and/or sealing composition (not shown here). The diameter of the tooth replacement support 7 decreases from the mating surface 14 in the direction toward the opposite end. A recess 17, which is not rotationally symmetrical with respect to the axis KA, is located at that end of the anchor body 4 remote from the surface 5. This can also involve semicircular, pocket-like recesses (not shown here) in the manner of a self-tapping screw, which recesses interrupt the circuit of the final 5 to 10 thread turns and extend as far as the end of the anchor body 4. Three such pocket-like recesses can advantageously be provided uniformly about the circumference of the threaded end section of the anchor 4.

Figure 3:
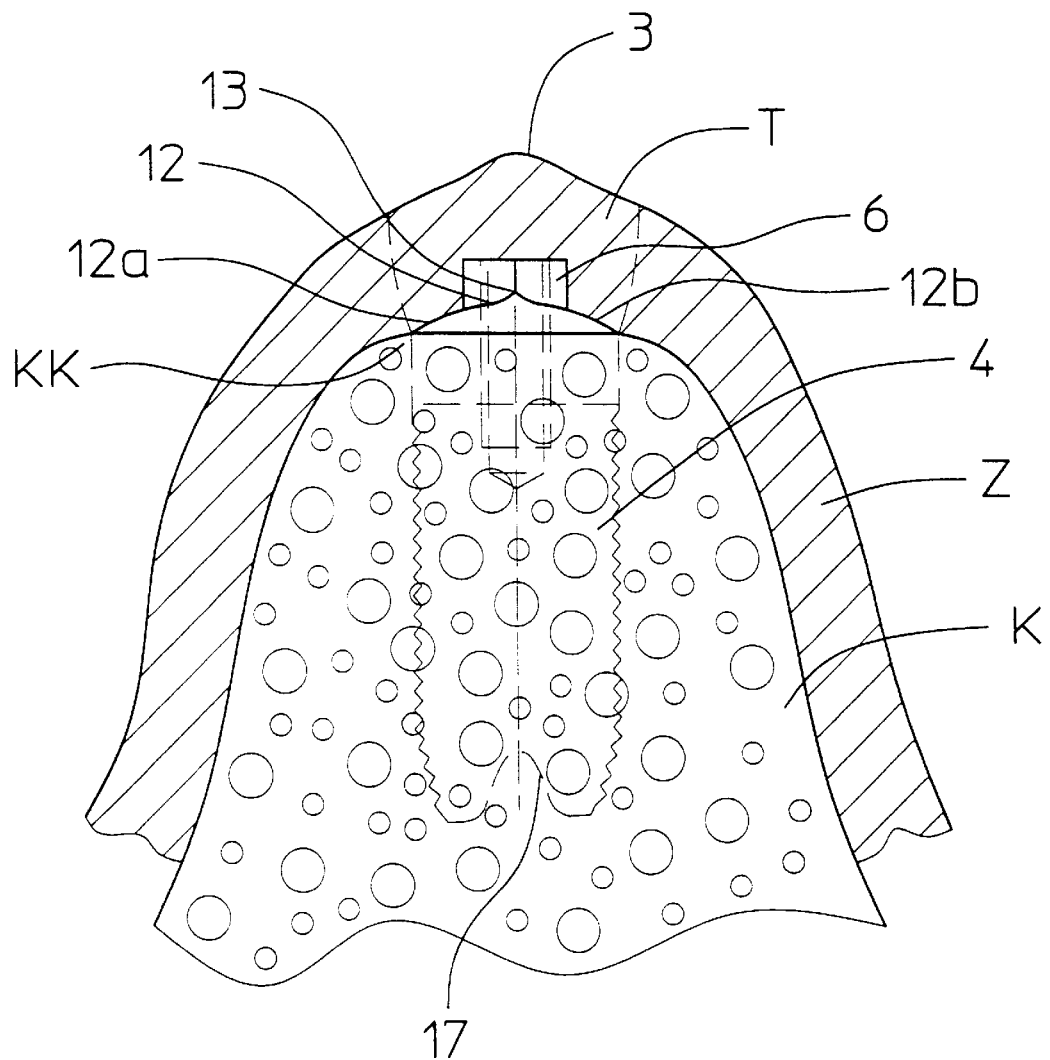
FIG. 3 shows a section along the line B—B in FIG. 1.

FIG. 3 shows a section along the line B—B in FIG. 1 [lacuna] the [sic] gum Z lying over the alveolar ridge KK forms a gingival pocket T in the area of the jaw implant 1. The gingival pocket T has the gingival elevation 3 in proximity to the alveolar ridge KK.

Figure 4:
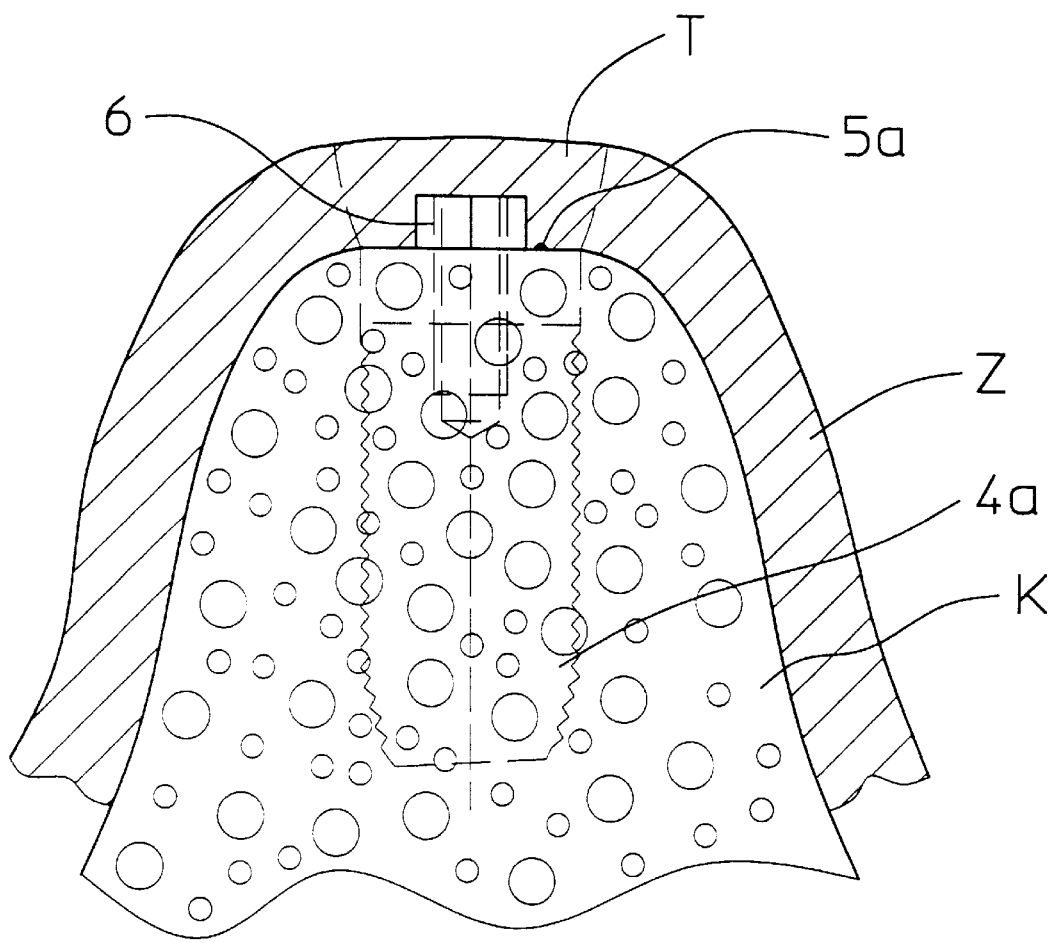
FIG. 4 shows a section along the line B—B in FIG. 1, with use of a conventional anchor element.

FIG. 4 shows the view according to FIG. 3, in this case with an anchor body 4a according to the prior art. Such an anchor body has a horizontal surface 5a. As will be seen from FIG. 4, when using anchor bodies 4a according to the prior art, the periodontally important gingival elevations do not form at the peripheral edge of the gingival pocket T.

The function of the jaw implant is as follows:

After the alveolar ridge KK has been exposed and a bore has been provided therein, the anchor element 4 is screwed into the jawbone K. To do this, a suitable screwing instrument is applied to the external hexagon profile 6. The anchor body 4 is screwed into the jawbone K in such a way that its crest 12 is in alignment with the alveolar ridge KK. The saddle of the surface 5 in this position complements the natural contour of the alveolar ridge KK. During incorporation, bone tissue grows through the recess 17 and the latter thus prevents the anchor body 4 from turning.

After the gingival pocket T has formed, the tooth replacement support 7 is secured on the anchor body 4 by means of the compression anchor screw 8. The tooth crown 10 is then mounted on the tooth replacement support 7. The circumferential edge 16 of the tooth crown 10 then lies on the circumferential projection 15 of the tooth replacement support 7. The circumferential projection 15 forms the maximum diameter D1 of the tooth replacement support 7. This corresponds approximately to the diameter D2 of the surface 5. By means of the design of the tooth replacement support 7, in particular the relation of its maximum diameter to the anchor body 4, the purchase on the tooth crown 10 in the event of an impact are minimized. This improves the hold of the jaw implant 1.

| List of reference labels | |
|---|---|
| 1 | Jaw implant |
| 2 | Tooth |
| 3 | Gingival elevation |
| 4 | Anchor body |
| 4a | Anchor body according to the prior art |
| 5 | Surface |
| 5a | Horizontal surface |
| 6 | External hexagon profile |
| 7 | Tooth replacement support |
| 8 | Threaded bore |
| 9 | Compression anchor screw |
| 10 | Tooth crown |
| 11 | External thread |
| 12 | Crest |
| 12a, 12b | Flanks |
| 13 | Further crest |
| 14 | Mating surface |
| 15 | Circumferential projection |
| 16 | Circumferential edge |
| 17 | Recess |
| Z | Gum |
| H | Height |
| D1 | Maximum diameter of the tooth replacement support |
| D2 | Maximum diameter of the surface |
| KA | Axis |
| KK | Alveolar ridge |
| K | Jawbone |
| T | Gingival pocket |

I claim:

1. Subgingival jaw implant with anchor body (4) which is made of metal material and at whose one end there is a surface (5) which is provided with a profile for engagement of a screwing instrument and on which a tooth replacement support (7) with a corresponding mating surface (14) can be supported, characterized in that the surface (5) has a first crest (12) and two flanks (12a, 12b) descending therefrom, in such a way that the anchor body (4) is screwable into the jawbone so the first crest (12) is in alignment with the alveolar ridge (KK) and the surface in this position complements the natural contour of the alveolar ridge (KK), and a second crest (13) provided on the first crest (12) and the maximum diameter (D1) of the tooth replacement support is equal to or smaller than the maximum diameter (D2) of the surface.

2. Subgingival jaw implant according to claim 1, in which the profile is an internal or external hexagon profile (6).

3. Subgingival jaw implant according to one of the preceding claims, in which a threaded bore (8) having a longitudinal axis (KA) is provided within the profile in order to receive a screw (9) for securing the tooth replacement support (7) on the anchor body (4).

4. Subgingival jaw implant according to claim 3, in which the crest (12) stands perpendicular to the axis (KA) of the threaded bore (8).

5. Subgingival jaw implant according to claim 4, in which the flanks (12a, 12b) descend from the crest (12) at an angle of 10 to 20°.

6. Subgingival jaw implant according to claim 5, in which the crest (12) and the flanks (12a, 12b) are constituent parts of an arch of the surface (5).

7. Subgingival jaw implant according to claim 3, in which a recess (17), which is not rotationally symmetrical with respect to the axis (KA), is located at that end of the anchor body (4) remote from the surface (5).

8. Subgingival jaw implant according to claim 1, in which a projection is provided on one of the flanks (12a, 12b).

9. Subgingival jaw implant according to claim 1, in which the tooth replacement support (7) has, at a first end, a mating surface (14) corresponding to the surface (5).

10. Subgingival jaw implant according to claim 9, in which the mating surface (14) has a recess corresponding to the further crest (13).

11. Subgingival jaw implant according to claim 9, in which the mating surface (14) has a further recess corresponding to the projection.

12. Subgingival jaw implant according to claim 1, in which the tooth replacement support (7) has, in proximity to the mating surface (14), a projection (15) extending at least in sections.

13. Subgingival jaw implant according to claim 12, in which the diameter of the tooth replacement support (7) decreases from a first end in proximity to the mating surface (14) toward a second end.

14. Subgingival jaw implant according to claim 1, in which an external thread (11), tapering conically in the direction of the other end, is provided at least in sections on the outside of the anchor body (4) for the purpose of engagement in the jawbone (K).

15. Subgingival jaw implant according to claim 1, in which the metal material is titanium or stainless steel.

* * * * *